United States Patent [19]

Terayama

[11] Patent Number: 4,471,766
[45] Date of Patent: Sep. 18, 1984

[54] RING APPLICATOR WITH AN ENDOSCOPE

[75] Inventor: Toshiki Terayama, Tokyo, Japan

[73] Assignee: InBae Yoon, Phoenix, Md.

[21] Appl. No.: 41,337

[22] Filed: May 22, 1979

[30] Foreign Application Priority Data

Nov. 24, 1977 [JP] Japan .................... 52-157602

[51] Int. Cl.³ .................................... A61B 17/12
[52] U.S. Cl. ......................... 128/6; 128/303 A; 128/326
[58] Field of Search .................. 128/3–8, 128/326, 303 A, 321, 320, 328, 325

[56] References Cited

U.S. PATENT DOCUMENTS

| | | | |
|---|---|---|---|
| 3,870,048 | 3/1975 | Yoon | 128/6 |
| 3,911,923 | 10/1975 | Yoon | 128/303 A |
| 4,085,743 | 4/1978 | Yoon | 128/303 A |
| 4,103,680 | 8/1978 | Yoon | 128/303 A X |

FOREIGN PATENT DOCUMENTS 2330182  1/1975  Fed. Rep. of Germany ...... 128/326

Primary Examiner—Michael H. Thaler
Attorney, Agent, or Firm—Robert E. Bushnell

[57] ABSTRACT

A ring applicator with an endoscope comprises an operation unit, an outer tube connected to the operation unit, an inner tube reciprocably inserted into the outer tube, an endoscope reciprocably inserted into the inner tube, a normally opening forceps consisting of a pair of hook-like strips secured to the distal end of the endoscope, a rubber ring mounted on the distal end portion of the inner tube, and an operation device provided at the operation unit for drawing back the endoscope only at first and then both the endoscope and the inner tube. Only by operating the operation device the rubber ring can be fed into a body cavity to clamp tissues in the body cavity, while the interior of the body cavity is being observed through the endoscope which is provided in the applicator.

5 Claims, 5 Drawing Figures

RING APPLICATOR WITH AN ENDOSCOPE

BACKGROUND OF THE INVENTION

This invention relates to a ring applicator with an endoscope incorporated in it.

Known ring applicators have themselves no means for observing the interior of a body cavity. It is therefore necessary to insert such a ring applicator into an extremely thick channel of an endoscope or to cut tissue layers or the wall of the living body to make an opening and insert an endoscope through the opening, thereby to observe the interior of a body cavity. To avoid these relatively intricate operations, an endoscope may be incorporated into the ring applicator. If this measure is adopted, however, the ring applicator will have too large a diameter or will become difficult to operate.

SUMMARY OF THE INVENTION

It is an object of this invention is to provide a ring applicator with an endoscope, which is simple in construction, has a small outer diameter and is easy to operate.

According to this invention there is provided a ring applicator with an endoscope, which comprises an operation unit, an outer tube secured at one end coaxially to one end of the operation unit; an inner tube inserted in the outer tube and having one end reciprocatively movable to alternatively come out of, and retreat into, the other end of the outer tube; a rubber ring removably mounted on the outer periphery of said one end of the inner tube; an endoscope inserted in the inner tube and movable reciprocatively relative to the inner tube lengthwise thereof; a forceps comprising a pair of hook-shaped strips secured at a proximal end thereof to the outer periphery of the distal end of the endoscope, disposed diametrically opposite with respect to the axis of the endoscope and normally biased outward radially of the endoscope; and an operation device mounted on the operation unit, which, when moved toward the other end of the operation unit, moves the endoscope through the inner tube toward the other end of the operation unit until the forceps is drawn into the inner tube to be closed and thereafter moves both the endoscope and the inner tube toward the other end of the operation unit until the outer tube pushes to remove the rubber ring from the inner tube.

BRIEF DESCRIPTION OF THE DRAWING

This invention can be fully understood from the following description with reference to the accompanying drawings in which.

DESCRIPTION OF THE PREFERRED EMBODIMENT

Figure 1:
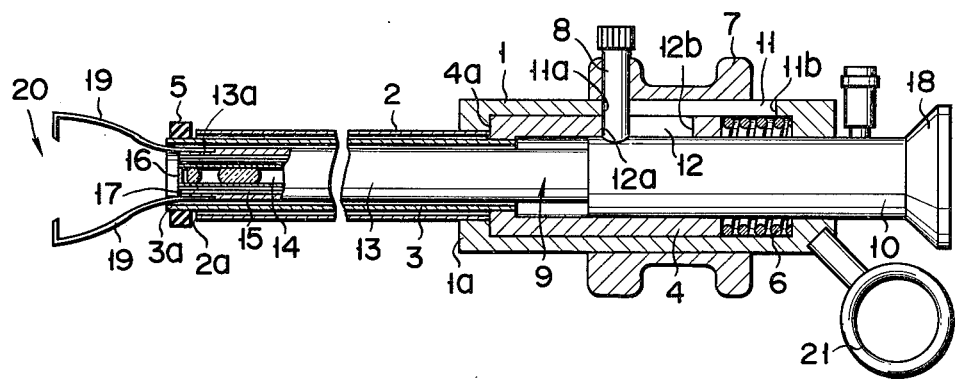
FIG. 1 is a longitudinal sectional view of a ring applicator according to this invention.

As shown in FIG. 1, a ring applicator of this invention comprises a hollow cylindrical operation unit 1, an outer tube 2 having the proximal end secured coaxially to the distal end of the operation unit 1, and an inner tube 3 reciprocatively inserted in the outer tube 2. The inner tube 3 has its proximal end connected to the distal end of a hollow cylindrical inner slider 4 which is reciprocatively movable in the operation unit 1. The inner tube 3 and the slider 4 can therefore move jointly. This inner slider 4 is always biased toward the distal end of the applicator by means of a coil spring 6 which is disposed in the operation unit 1. In the leftmost position, the distal end 4a of the slider 4 is in contact with an inwardly extending flange 1a integrally formed with the distal end of the operation unit 1. When the inner slider 4 is at the leftmost position, a distal end portion 3a of the inner tube 3 protrudes for a predetermined distance from a distal end 2a of the outer tube 2 such that a rubber ring 5 for clamping tissues is removably mounted on the periphery of the protruded distal end portion 3a. Normally, the slider 4 stays in the leftmost position as shown in FIG. 1. On the outer periphery of the operation unit 1, a ring-shaped operation slider 7 is slidably mounted.

The ring applicator further comprises an endoscope 9. The endoscope 9 comprises a hollow cylindrical proximal end portion 10 and a tubular distal end portion 13. The proximal end portion 10 is reciprocatingly inserted in the slider 4. The distal end portion 13 has a smaller diameter than the proximal end portion 10 and is inserted partly in the slider 4 and mostly in the inner tube 3.

The operation unit 1 has an elongated hole 11 extending in its lengthwise direction. Similarly, the slider 4 has an elongaged hole 12 extending in its lengthwise direction. The distal end 11a of the hole 11 is aligned with the distal end 12a of the hole 12. The proximal end 11b of the hole 11 is nearer to the proximal end of the applicator than the proximal end 12b of the hole 12. A pin 8 penetrates the operation slider 7 and the elongated holes 11 and 12. Its inner end is removably inserted in a hole made in the proximal end portion 10 of the endoscope 9 or makes screw engagement with a female screw formed in the proximal end portion 10. The pin 8 therefore connects the slider 7 to the proximal end portion 10 of the endoscope 9.

As the operation slider 7 is pulled toward the proximal end of the applicator, the pin 8 hits the proximal end 12b of the elongated hole 12 of the slider 4 and thereafter pushes the slider 4 toward the proximal end of the applicator. The slider 4 can be moved in this direction until the pin 8 contacts the proximal end 11b of the elongated hole 11 of the operation unit 1.

When the endoscope 9 is in its extreme left position, its distal end is disposed at the distal end of the applicator.

Figure 2:
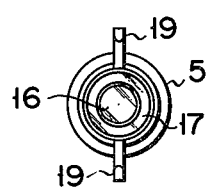
FIG. 2 is a front view of the distal end portion of the applicator shown in FIG. 1.

Through the central portion of the distal end portion 13 of the endoscope 9, an observation light guide 14 extends. An illumination light guide 15 coaxially surrounds the observation light guide 14 and also extends through the distal end portion 13. As shown in FIGS. 1 and 2, the distal end of the distal end portion 13, which is located at the distal end of the inner tube 3, has an observation window 16 and an illumination window 17 surrounding the window 16. These windows 16 and 17 are optically coupled to the light guides 14 and 15, respectively. As conventionally practiced, illumination light guided to the light guide 15 via a bundle of optical fibers (not shown) from a light source (not shown) provided outside the endoscope 9. The illumination light is then transmitted to the illumination window 17 through the light guide 15, thus illuminating the interior of a body cavity. The interior of the body cavity is observed through the observation window 16, the light guide 14 and an eyepiece 18 attached to the proximal end portion 10 of the endoscope 9.

Figure 3:
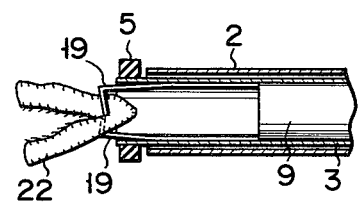
FIG. 3 shows a forceps of the ring applicator shown in FIG. 1, which is now holding an oviduct.

A pair of forceps strips 19 are secured at their proximal end to the outer periphery of the end 13a of the distal end portion 13, disposed diametrically opposite with respect to the axis of the endoscope 9. The strips 19 are biased outward in the radial direction of the applicator so that they constitute a normally open forceps 20. That is, the forceps 20 opens so long as it protrudes from the distal ends of both the outer tube 2 and the inner tube 3 as shown in FIG. 1. When the distal end portion 13 of the endoscope is drawn toward the proximal end of the operation unit 1, the forceps 20 is pulled into the inner tube 3 and is closed as shown in FIG. 3.

Now it will be described how to operate the ring applicator of the above-mentioned construction.

Figure 4:
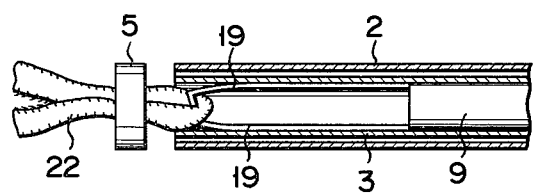
FIG. 4 illustrates a rubber ring removed from an inner tube of the applicator shown in FIG. 1 and clamping an oviduct.

First, the operation slider 7 is pulled toward the proximal end of the operation unit 1 until it comes in contact with the proximal end 12b of the elongated hole 12 of the slider 4 and the forceps 20 is pulled in the distal end portion of the inner tube 3. Then, the outer tube 2 of the applicator is inserted into a body cavity through a trocar or an insertion channel of another endoscope. This done, the operation slider 7 is pushed toward the distal end of the operation unit 1, thereby pushing the endoscope 9 farther into the body cavity until the forceps 20 comes out of the inner tube 3 and fully opens as shown in FIG. 1. While observing the interior of the body cavity through the endoscope 9, the operator moves the applicator farther into the body cavity until an oviduct 22 is disposed between its strips 19. Then, he inserts his finger into, or applies his finger to a ring holder 21 attached to the proximal end portion of the operation unit 1 and pushes the operation unit 1 farther into the body cavity. The outer tube 2 is thus moved in the same direction as that of the operation unit 1 without moving the endoscope 9, the slider 4 and the inner tube 3 connected to the slider 4. As the outer tube 2 is moved together with the operation unit 1 farther into the body cavity until the pin 8 hits the proximal end 12b of the elongated hole 12 of the slider 4, the forceps 20 is pulled into the inner tube 3 and the oviduct 22 is held and pulled into the inner tube 3 by the forceps 20. As the operation unit 1 is moved forward further, the slider 4 is moved rearward jointly therewith until the pin 8 abuts against the proximal end 11b of the hole 11 in the operation unit 1. During this movement of the slider 4, the inner tube 3, which is connected to the slider 4, is moved farther toward the proximal end of the operation unit 1 with respect to the outer tube 2 with the result that the rubber ring 5, which has been mounted on the distal end portion of the inner tube 3, is pushed by the distal end 2a of the outer tube 2 to be removed from the inner tube 3 and finally clamps the oviduct 22 as shown in FIG. 4.

Figure 5:
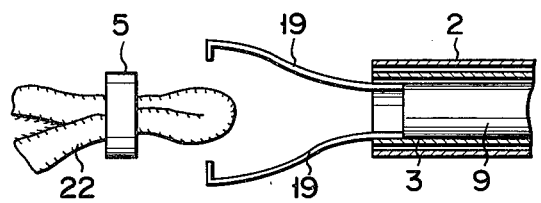
FIG. 5 illustrates an oviduct clamped by an rubber ring.

Thereafter, the operation slider 7 is pushed toward the distal end 1a of the operation unit 1. The forceps 20 protrudes from the distal end 3a of the inner tube 3 and then is opened to release the oviduct 22 clamped by the rubber ring 5, as shown in FIG. 5. Then, the operation slider 7 is pulled to the proximal end of the operation unit 1 thereby to pull the forceps 20 into the inner tube 3. Then, the applicator is pulled out of the body cavity, thus completing the ring application.

As mentioned above, the operation slider 7 is moved back and forth with respect to the operation unit 1, thereby causing the forceps 20 to hold the oviduct 22 and the rubber ring 5 to clamp the oviduct 22. In other words, a single member serves to achieve two operations, whereas a forceps is actuated by one member and a rubber ring is mounted on a tissue by another member in the known ring applicator. In addition, these operations are carried out, while the interior of the body cavity is observed through the endoscope 9 provided in the applicator. The operations can therefore be achieved very safely and very quickly. Moreover, since the strips 19 of the forceps 20 are secured to the outer periphery of the distal end portion 13 of the endoscope 9, the optical system for observing the interior of a body cavity can occupy all the space provided in the distal end portion 13 of the endoscope 9. Thus, the diameter of the outer tube 2 can be made thinner.

What is claimed is:

1. A ring applicator with an endoscope, comprising:
   an operation unit having two opposite ends;
   an outer tube having one end coaxially secured to one end of said operation unit and the other end open;
   an inner tube reciprocably inserted into said outer tube and having two ends, one end being normally biased to protrude from and to be drawn into said other end of said outer tube and the other end being open;
   a rubber ring removably mounted on an outer periphery of said one end of said inner tube;
   an endoscope reciprocably inserted into said inner tube and having a distal end and a proximal end;
   a forceps comprising a pair of hook-shaped strips each secured at one end thereof to an outer periphery of said distal end of said endsocope, disposed diametrically of said endoscope and normally biased outward radially of said endoscope; and
   an operation device slidably mounted on said operation unit and having a distal end connected to said endoscope and operatively engageable with said other end of said inner tube, said operation device being operable to pull said endoscope through said inner tube toward said other end of said operation unit until said forceps is drawn into said inner tube and is closed and then to move both said endoscope and said inner tube toward said other end of said operation unit until said outer tube pushes and removes said rubber ring from said tube, as said operation device is being moved toward said other end of said operation unit.

2. The ring applicator according to claim 1, wherein said operation device comprises;
   an operation slider surrounding said operation unit and slidable axially thereof, and having an elongated hole lengthwise formed in the operation unit; and
   a pin penetrating the elongated hole for connecting the proximal end of the endoscope to the operation slider and to said inner tube.

3. The ring applicator according to claim 2, wherein said operation device further comprises:
   an inner slider surrounding the endoscope slidably lengthwise of the endoscope;
   an elongated hole formed in the inner slider, extending lengthwise of the operation unit and having one end which is nearer to said other end of the operation unit arranged to engage the pin when the endoscope is moved toward said other end of the operation unit and the forceps is closed; and biasing means provided in the operation unit for urging the inner slider toward said one end of the operation unit.

4. The ring applicator according to claim 3, further comprising a ring holder which is attached to said other end of said operation unit and to which a finger is applied.

5. The ring applicator according to any one of the preceding claims, wherein said pin is removable.

* * * * *